United States Patent [19]

Cook

[11] Patent Number: 5,278,339
[45] Date of Patent: Jan. 11, 1994

[54] PROCESS FOR THE RECOVERY OF CYCLOHEXANEDICARBOXYLIC ACIDS

[75] Inventor: Steven L. Cook, Kingsport, Tenn.

[73] Assignee: Eastman Kodak Company, Rochester, N.Y.

[21] Appl. No.: 24,018

[22] Filed: Mar. 1, 1993

[51] Int. Cl.$^5$ .............................................. C07C 61/09
[52] U.S. Cl. .................................................... 562/509
[58] Field of Search ........................................ 562/509

[56] References Cited

U.S. PATENT DOCUMENTS

| | | | |
|---|---|---|---|
| 4,221,871 | 9/1980 | Meitzner et al. | 521/29 |
| 4,224,415 | 9/1980 | Meitzner et al. | 521/38 |
| 4,256,840 | 3/1981 | Meitzner et al. | 521/33 |
| 4,297,220 | 10/1981 | Meitzner et al. | 210/690 |
| 4,382,124 | 5/1983 | Meitzner et al. | 521/38 |

OTHER PUBLICATIONS

Reillex TM Report 2, Reilly Industries, Inc., 1510 Market Square Center, 151 N. Delaware Street, Indianapolis, Indiana 46204 (1990).
Reillex TM Report 3, Reilly Industries, Inc., 1510 Market Square Center, 151 N. Delaware Street, Indianapolis, Indiana 46204 (1989).
Reillex TM Report 4, Reilly Industries, Inc., 1510 Market Square Center, 151 N. Delaware Street, Indianapolis, Indiana 46204 (1989).
Reillex TM Report 5, Reilly Chemicals, SA, Rue Defacqz, Boite 19, B-1050 Bruxelles, Belgium.
Reillex TM Report 6, Reilly Industries, Inc., 1510 Market Square Center, 151 N. Delaware Street, Indianapolis, Indiana 46204 (1989).

*Primary Examiner*—Michael L. Shippen
*Attorney, Agent, or Firm*—J. Frederick Thomsen; William P. Heath, Jr.

[57] ABSTRACT

Disclosed is a process for the recovery of a cyclohexanedicarboxylic acid from an aqueous solution of the cyclohexanedicarboxylic acid and sodium sulfate by contacting the solution with vinylpyridine/divinylbenzene ion exchange resins.

5 Claims, No Drawings

PROCESS FOR THE RECOVERY OF CYCLOHEXANEDICARBOXYLIC ACIDS

This invention pertains to a process for the recovery of a cyclohexanedicarboxylic acid from an aqueous solution of the cyclohexanedicarboxylic acid and sodium sulfate by contacting the solution with certain ion exchange resins.

U.S. Pat. No. 5,118,841 describes a process for the preparation of cyclohexanedicarboxylic acids wherein the disodium salt of a benzenedicarboxylic acid is hydrogenated in the presence of certain catalysts to produce the corresponding disodium cyclohexanedicarboxylate which is then treated with sulfuric acid to produce the cyclohexanedicarboxylic acid. This process produces a waste stream comprising an aqueous solution of sodium sulfate and a minor amount of the cyclohexanedicarboxylic acid product. The presence of the cyclohexanedicarboxylic acid in the waste stream is undesirable since it represents a loss in the overall yield of the manufacturing process and also increases the load on the waste water treatment plant which processes the waste stream.

It is generally known to selectively adsorb a specific component from a waste stream, especially an acid from an otherwise neutral stream, by means of ion exchange resins. Thus, it was thought that some type of weakly basic ion exchange resin would work by selectively reacting with the acidic carboxylic acid groups of the cyclohexanedicarboxylic acid. Weakly basic ion exchange resins typically comprise polymers containing pendant phenyl groups bearing a tertiary amino radicals, e.g., dialkylaminophenyl and dialkylaminomethylphenyl groups. Apparently, such selective reaction is easy to accomplish if the stream consists essentially of the cyclohexanedicarboxylic acid and water. A complicating factor, however, is the presence in the solution of relatively high concentrations, e.g., about 10 to 20 weight percent, of sodium sulfate ($Na_2SO_4$). As a result, the cyclohexanedicarboxylic acid that is adsorbed initially by the resin through the formation of a protonated amine carboxylate complex, can be displaced by the sulfate group, forming an amine sulfate complex and a sodium carboxylate salt which elutes from the resin.

I have discovered that a cyclohexanedicarboxylic acid can be removed selectively from an aqueous solution of the cyclohexanedicarboxylic acid and sodium sulfate by contacting the solution with an ion exchange resin wherein the ion exchange functionality comprises residues of vinylpyridine. The present invention therefore provides a process for the recovery of cyclohexanedicarboxylic acid from an aqueous solution of the cyclohexanedicarboxylic acid and sodium sulfate by the steps of:

(1) contacting the solution with an ion exchange resin wherein the ion exchange functionality comprises residues of vinylpyridine; and (2) obtaining the aqueous solution depleted in its content of the cyclohexanedicarboxylic acid.

Basic ion exchange copolymers derived from vinyl pyridine and divinylbenzene have been used to remove phenolic impurities in hydrogen peroxide (U.S. Pat. No. 4,975,266) and to recover phenols (German Patent 2,947,765), recover carboxylic acids (German Patent 3,043,766 and in American Laboratory, 92, 94-9 (1990)), remove iodine (Japanese Patent 51148693, 50113560), and remove sulfur dioxide from air (German Patent 2,164,261). It is also useful for chromium adsorption (Japanese Patent 51114389). The prior art does not disclose or teach that such vinylpyridine/divinylbenzene copolymers would exhibit selectivity for adsorbing a dicarboxylic acid in the presence of concentrated aqueous sodium sulfate solutions.

The aqueous solution used in the process of my invention may contain about 10 to 20 weight percent, more typically about 13 to 15 weight percent, sodium sulfate and about 0.5 to 1.5 weight percent of a cyclohexanedicarboxylic acid. The ion exchange resin normally is in the form of beads or particles of sufficient size to permit the aqueous solution to pass over and through one or more beds of the particles. A sphere size of 18 to 50 mesh is typical. The contact time between the solution being treated and the ion exchange resin normally should be at least 60 seconds and usually is in the range of about 5 to 10 minutes. The process permits the adsorption or recovery of at least 70, preferably from about 75 to 85, weight percent of the cyclohexanedicarboxylic acid present in the solution fed to the process.

The process may be carried out at a temperature of about 20° to 90° C., preferably about 30° to 60° C. The process may be utilized to recover any of the isomers of cyclohexanedicarboxylic acid although its use most commonly will concern the recovery of 1,3- and, especially, 1,4-cyclohexanedicarboxylic acid.

As is apparent to those skilled in the art, it is necessary to "regenerate" the pyridine-containing ion exchange resin by contacting it with a solution of a base such as an aqueous solution of an alkali metal hydroxide or carbonate, especially sodium hydroxide. Thus, a second embodiment of the present invention pertains to a process for the recovery of cyclohexanedicarboxylic acid values as disodium cyclohexanedicarboxylate from an aqueous solution containing sodium sulfate and cyclohexanedicarboxylic acid and sodium sulfate by the steps of:

(1) contacting the solution with a vinylpyridine/divinylbenzene ion exchange resin; and (2) treating the ion exchange resin resulting from step (1) with an aqueous sodium hydroxide solution. The concentration of the alkali metal compound in the regenerating solution may be from about 2 to 20 weight percent. The amount of the alkali-containing regeneration solution employed may be in the range of 1 to 20 parts by weight of regeneration solution per part by weight of ion exchange resin. The contact time between the ion exchange resin and the regeneration solution normally is at least 60 seconds, usually from about 5 to 10 minutes. The cyclohexanedicarboxylic acid adsorbed by the ion exchange resin is desorbed by the regeneration solution and converted to its disodium salt. The concentration of the disodium cyclohexanedicarboxylate in the aqueous solution recovered from the regeneration step may be from about 1 to 10 weight percent. This solution of disodium cyclohexanedicarboxylate can be returned directly to the cyclohexanedicarboxylic acid manufacturing process described above, thus allowing recovery of the valuable product and the elimination of a waste stream.

The process of the present invention is further illustrated by the following examples. All of the examples were performed on a simulated cyclohexanedicarboxylic acid/sodium sulfate waste stream. This simulated waste stream was prepared by stirring overnight at room temperature an excess (40 g) of 1,4-cyclohexanedicarboxylic acid with a solution of 260 g of reagent grade sodium sulfate in 1740 g of water and then filtering. The filtrate was assayed for 1,4-cyclohexanedicarboxylic acid content via titration using phenolphthalein and 0.1 N sodium hydroxide solution. The filtrate (simulated waste stream) was found to contain 0.89 weight percent 1,4-cyclohexane-dicarboxylic acid.

With the starting concentration of 1,4-cyclohexanedicarboxylic acid established, an internal standard gas chromatography method was developed to analyze the treated solutions. A 1 weight percent disodium terephthalate solution was used as the internal standard via the following procedure: A stock solution of 1 weight percent disodium terephthalate in water was prepared by mixing 1.0 g of terephthalic acid with 99.0 g of water. To this was added 0.5 g of reagent grade sodium hydroxide pellets. The pH was checked to verify that the pH wa slightly basic and visual inspection used to confirm the absence of any undissolved solid. The 10.0 g of the stock, solution was added 1.0 g of the internal standard. The pH of this solution was adjusted to $\leq 2$ with several drops of concentrated sulfuric acid. This solution was placed on a rotary evaporator and stripped to dryness at reduced pressure (20 torr final pressure, 70° C. bath temperature). To the residue was added 2 mL of reagent grade pyridine. After swirling periodically over a one minute period, 10 drops of this solution was transferred to a small septum bottle which was capped and evacuated via a 10 cc syringe. To the sample was added 0.25 mL of BSTFA silylating reagent. The mixture was heated at 80° C. for 10 minutes, cooled, and the vacuum released via a gc syringe. A 4 $\mu$L sample of this solution was injected onto an HP 5890A gas chromatograph fitted with a 60 meter DX4 column. Peak elution was detected via a flame ionization detector. Test samples were analyzed via the same method in that 10.0 g samples were used in combination with 1.0 g of the disodium terephthalate internal standard.

EXAMPLE 1

A mixture of 20 g of the above-described, simulated waste stream and 1.0 g of a 4-vinylpyridine/divinylbenzene ion exchange resin marketed under the name Reilex 425 was stirred by means of a magnetic stir bar for 1 hour at room temperature. The mixture was filtered to remove the ion exchange resin and analysis of the filtrate showed that it contained 0.46 weight percent 1,4-cyclohexanedicarboxylic acid. This procedure was repeated using 2.5, 5.0 and 10.0 g of the same ion exchange resin to give filtrates containing 0.24, 0.17 and 0.09 weight percent 1,4-cyclohexanedicarboxylic acid, respectively.

COMPARATIVE EXAMPLE 1

A mixture of 20 g of the above-described, simulated waste stream and 1.2 g of a styrene-divinylbenzene copolymer containing a dimethylamino functional group, a weakly basic ion exchange resin marketed under the name Amberlyst A-21, was stirred by means of a magnetic stir bar for 1 hour at room temperature. The mixture was filtered to remove the ion exchange resin and analysis of the filtrate showed that it contained 0.58 weight percent 1,4-cyclohexanedicarboxylic acid. This procedure was repeated using 2.4 and 4.8 g of the same ion exchange resin to give filtrates containing 0.65 and 0.60 weight percent 1,4-cyclohexanedicarboxylic acid, respectively. When this procedure was repeated using 4.8 g of the same ion exchange resin and contact time of 12 hours, the resulting filtrate contained 0.53 weight percent 1,4-cyclohexanedicarboxylic acid.

COMPARATIVE EXAMPLE 2

A mixture of 20 g of the above described, simulated waste stream and 1.3 g of a styrene resin containing a trimethylammonium salt functional group, a strongly basic ion exchange resin marketed under the name Amberlyst A-26, was stirred by means of a magnetic stir bar for 1 hour at room temperature. The ion exchange resin employed was pretreated with excess sodium hydroxide overnight followed by filtration and washing with excess water to put the resin in the hydroxyl form. The mixture was filtered to remove the ion exchange resin and analysis of the filtrate showed that it contained 0.70 weight percent 1,4-cyclohexanedicarboxylic acid. This procedure was repeated using 2.6, 5.0 and 10.0 g of the same ion exchange resin to give filtrates containing 0.58, 0.51 and 0.37 weight percent 1,4-cyclohexanedicarboxylic acid, respectively.

COMPARATIVE EXAMPLE 3

A mixture of 20 g of the above described, simulated waste stream and 5.0 g of an epichlorohydrin/ammonia copolymer quaternized with methyl chloride, a weakly basic, epoxy-amine resin marketed under the name Dow WGR-2, was stirred by means of a magnetic stir bar for 1 hour at room temperature. The mixture was filtered to remove the ion exchange resin and analysis of the filtrate showed that it contained 0.75 weight percent 1,4-cyclohexanedicarboxylic acid.

COMPARATIVE EXAMPLE 4

A mixture of 20 g of the above described, simulated waste stream and 5.0 g of a macroporous styrene divinylamine copolymer, a weakly basic ion exchange resin marketed under the name Dow M 43, was stirred by means of a magnetic stir bar for 1 hour at room temperature. The mixture was filtered to remove the ion exchange resin and analysis of the filtrate showed that it contained 0.61 weight percent 1,4-cyclohexanedicarboxylic acid.

COMPARATIVE EXAMPLE 5

A mixture of 20 g of the above described, simulated waste stream and 5.0 g of a proprietary amine type resin, a basic ion exchange resin marketed under the name Technichem TCA-114M, was stirred by means of a magnetic stir bar for 1 hour at room temperature. The mixture was filtered to remove the ion exchange resin and analysis of the filtrate showed that it contained 0.61 weight percent 1,4-cyclohexanedicarboxylic acid.

It is apparent from the above examples that the vinylpyridine/divinylbenzene ion exchange resins sold under the names Reilex 425 and Polysorb MP2 are substantially more effective than other types of ion exchange resins in removing 1,4-cyclohexanedicarboxylic acid from solutions containing the diacid and a significant amount of sodium sulfate.

The vinylpyridine/divinylbenzene ion exchange resin (Reilex 425) was further evaluated by the assembly of apparatus in which a fixed bed of the resin was used. The bed was contained within a vertical, glass tube 1.22 meters in length and having an inside diameter of 22 mm. The bottom of the tube was sealed with a rubber stopper fitted with an exit line which was connected to a peristaltic pump which removed liquid from the tube at a constant rate.

The above described, simulated waste stream was fed to the top of the tube by means of a peristaltic pump. The level of the feed solution was maintained above the top of the resin bed with the flow being controlled by a Thermowatch controller which switched the peristaltic pump on and off as necessary to maintain the level of solution in the tube. Flow rate requirements for some experiments required that the pumps be operated with four silicone tubes passed through the appropriate slots in the pump head. This modification permitted feed to the column at a rate up to four times that of a single line. Electrical tracing around the resin-containing section of the bed was provided so that some limited work at elevated column temperatures could be performed. The bed temperature, however, may not have been entirely uniform via this arrangement.

EXAMPLE 2

A vinylpyridine/divinylbenzene ion exchange resin (71 g, Reilex 425) was place in the glass tube of the above described apparatus. After the resin had become wetted, it occupied a bed volume of 230 mL. The simulated waste stream was fed to the resin bed at a rate of 389 mL per hour (6.5 mL/minute, 0.028 L/minute per L of resin). The bed temperature was 23°-24° C. Samples of the effluent removed from the bed were taken and analyzed periodically. The results are shown below wherein "mL Fed" refers to the amount of the simulated waste stream which had been fed to the tube at the time the particular sample was taken and "% CHDA" is the weight percent concentration of 1,4-cyclohexanedicarboxylic acid present in the particular sample taken and analyzed.

| mL Fed | % CHDA |
|---|---|
| 120 | 0.10 |
| 240 | 0.16 |
| 360 | 0.15 |
| 480 | 0.23 |
| 600 | 0.16 |
| 720 | 0.13 |
| 840 | 0.13 |
| 1000 | 0.18 |
| 1120 | 0.19 |
| 1240 | 0.24 |
| 1360 | 0.19 |
| 1515 | 0.22 |
| 1635 | 0.17 |
| 1755 | 0.20 |
| 1875 | 0.17 |
| 1995 | 0.37 |
| 2125 | 0.23 |
| 2245 | 0.39 |
| 2365 | 0.45 |
| 2485 | 0.50 |
| 2605 | 0.68 |
| 2725 | 0.49 |
| 2845 | 0.46 |
| 3095 | 0.47 |
| 3215 | 0.69 |

EXAMPLE 3

The ion exchange resin bed employed in Example 2 was regenerated by contacting the resin with 1 liter of 5 weight percent aqueous sodium hydroxide solution for one hour at room temperature. This regeneration effluent contained 1.73 weight percent (16.7 g) of disodium cyclohexanedicarboxylate and weighed 965.8 g.

The procedure of Example 2 was repeated with a resin bed temperature of 24°-25° C. and a higher flow rate of 1470 mL per hour (24.5 mL/minute, 0.107 L/minute per L of resin). The results of analyses of samples taken periodically are shown below.

| mL Fed | % CHDA |
|---|---|
| 500 | 0.15 |
| 1000 | 0.42 |
| 1500 | 0.40 |
| 2000 | 0.48 |
| 2500 | 0.48 |
| 3465 | 0.77 |

EXAMPLE 4

The resin bed was regenerated as described in Example 3 and then the procedure of Example 2 was repeated with a resin bed temperature of 35° C. and a higher flow rate of 1310 mL per hour (21.8 mL/minute, 0.095 L/minute per L of resin). The bed temperature was controlled at 35° C. by means of a bed thermocouple connected to a controller which turned current on/off to Nichrome windings around the column. The results of analyses of samples taken periodically are shown below.

| mL Fed | % CHDA |
|---|---|
| 250 | 0.00 |
| 500 | 0.21 |
| 750 | 0.16 |
| 1000 | 0.17 |
| 1500 | 0.22 |
| 1750 | 0.27 |
| 2000 | 0.30 |
| 2250 | 0.29 |
| 2500 | 0.37 |
| 2750 | 0.37 |
| 3000 | 0.37 |
| 3250 | 0.58 |
| 3500 | 0.65 |
| 3630 | 0.86 |

The above Example 2-4 show that a pyridine based ion exchange resin is highly effective for the selective removal of cyclohexanedicarboxylic acid from a sodium sulfate brine solution. The first resin bed test was performed at a slow feed rate to insure adequate time for adsorption onto the resin. Analysis of the column effluent indicated that the initial cyclohexanedicarboxylic acid concentration of 0.89 to 0.90 weight percent was being reduced to constant levels averaging 0.16 weight percent. After apparent breakthrough, regeneration of the bed with 5% sodium hydroxide yielded 965.8 g of effluent that contained 1.73 weight percent disodium cyclohexanedicarboxylate (16.6 g). This indicates that the resin has a capacity of approximately 4.5 pounds per cubic foot. When the feed rate is increased by a factor of four, however, insufficient contact time occurs so that only 50 weight percent of the cyclohexanedicarboxylic acid was removed. If the bed is warmed by about 10° C., to a 35° C. operating temperature, performance nearly equal to that of the room temperature run at the slow feed rate is achieved. This observation indicates that a certain amount of contact time is required to permit selective removal of cyclohexanedicarboxylic acid to occur. As a check of the 4.5 pounds per cubic foot capacity value obtained above, a calculation of the cyclohexanedicarboxylic acid remaining in the effluent of the last run was performed. Breakthrough occurred rather quickly after approximately 3000 mL of material had been fed. The average cyclohexanedicarboxylic acid content in the effluent was 0.26 weight percent. The cyclohexanedicarboxylic acid removed from the 3000 mL of feed was, therefore, (0.89%−0.26%)×3000 g=18.9 g, for a capacity of 5.1 pounds per cubic foot, a value very close to the 4.5 pounds per cubic foot value derived from analysis of the cyclohexanedicarboxylic acid content in the dilute caustic bed wash.

The invention has been described in detail with particular reference to preferred embodiments thereof, but it will be understood that variations and modifications can be effected within the spirit and scope of the invention.

I claim:

1. Process for the recovery of cyclohexanedicarboxylic acid from an aqueous solution of the cyclohexanedicarboxylic acid and sodium sulfate by the steps of:
   (1) contacting the solution with an ion exchange resin wherein the ion exchange functionality comprises residues of vinylpyridine; and
   (2) obtaining the aqueous solution depleted in its content of the cyclohexanedicarboxylic acid.

2. Process according to claim 1 wherein the concentration of sodium sulfate is about 10 to 20 weight percent sodium sulfate and the concentration of the cyclohexane dicarboxylic acid is about 0.5 to 1.5 weight percent.

3. Process according to claim 1 wherein the concentration of sodium sulfate is about 13 to 15 weight percent sodium sulfate, the concentration of the cyclohexane dicarboxylic acid is about 0.5 to 1.5 weight percent, and the process is performed at a temperature of about 30° to 60° C.

4. Process for the recovery of cyclohexanedicarboxylic acid from an aqueous solution containing about 13 to 15 weight percent sodium sulfate and about 0.5 to 1.5 weight percent of the cyclohexanedicarboxylic acid and sodium sulfate by the steps of:
   (1) contacting the solution with a vinylpyridine/divinylbenzene ion exchange resin; and
   (2) obtaining the aqueous solution depleted in its content of the cyclohexanedicarboxylic acid.

5. Process for the recovery of cyclohexanedicarboxylic acid values as disodium cyclohexanedicarboxylate from an aqueous solution containing about 13 to 15 weight percent sodium sulfate and about 0.5 to 1.5 weight percent of the cyclohexanedicarboxylic acid and sodium sulfate by the steps of:
   (1) contacting the solution with a vinyl pyridine/divinylbenzene ion exchange resin; and
   (2) treating the ion exchange resin resulting from step (1) with an aqueous sodium hydroxide solution.

* * * * *